United States Patent
Singh et al.

(10) Patent No.: US 11,195,617 B1
(45) Date of Patent: Dec. 7, 2021

(54) INTELLIGENT TRIAGING ENGINE

(71) Applicant: WALGREEN CO., Deerfield, IL (US)

(72) Inventors: Atul Singh, Vernon Hills, IL (US);
Gregory Orr, Lake Bluff, IL (US);
Adam S. Pellegrini, Lake Forest, IL (US)

(73) Assignee: WALGREEN CO., Deerfield, IL (US)

( * ) Notice: Subject to any disclaimer, the term of this patent is extended or adjusted under 35 U.S.C. 154(b) by 444 days.

(21) Appl. No.: 15/348,681

(22) Filed: Nov. 10, 2016

Related U.S. Application Data (60) Provisional application No. 62/253,267, filed on Nov. 10, 2015.

(51) Int. Cl.
*G16H 50/20* (2018.01)
*G16H 80/00* (2018.01)
*H04L 29/08* (2006.01)
*G06F 19/00* (2018.01)

(52) U.S. Cl.
CPC ............ *G16H 50/20* (2018.01); *G06F 19/324* (2013.01); *G06F 19/3418* (2013.01); *G16H 80/00* (2018.01); *H04L 67/12* (2013.01)

(58) Field of Classification Search
CPC .... G16H 50/20; G06F 19/324; G16F 19/3418
USPC .......................................................... 705/2
See application file for complete search history.

(56) References Cited

U.S. PATENT DOCUMENTS

| | | | | |
|---|---|---|---|---|
| 2006/0020950 | A1* | 1/2006 | Ladd | H04L 63/168 719/328 |
| 2006/0161456 | A1* | 7/2006 | Baker | G06F 19/00 705/2 |
| 2010/0070303 | A1* | 3/2010 | Massoumi | G06Q 10/109 705/3 |
| 2010/0235295 | A1* | 9/2010 | Zides | G06Q 30/02 705/347 |
| 2011/0202361 | A1* | 8/2011 | Firminger | G06F 19/328 705/2 |
| 2013/0317842 | A1* | 11/2013 | Schoenberg | G06Q 30/02 705/2 |
| 2014/0019468 | A1* | 1/2014 | Federoff | G16H 50/20 707/758 |
| 2015/0229719 | A1* | 8/2015 | Sella | H04L 47/33 709/217 |
| 2017/0103171 | A1* | 4/2017 | Sentell | G06Q 30/0282 |

* cited by examiner

*Primary Examiner* — Aryan E Weisenfeld
*Assistant Examiner* — Karen A Hranek
(74) *Attorney, Agent, or Firm* — Marshall, Gerstein & Borun LLP; Randall G. Rueth (57) ABSTRACT

A method for intelligently triaging patients may be provided. The computer-implemented may diagnose a patient based up a received set of medical symptoms. In response, to the diagnosis, a filterable and/sortable list of healthcare service recommendations may be generated. The list of healthcare services may be generated based upon an analysis of a plurality of user data. Each recommendation on the list of healthcare service recommendations may correspond to a plurality of metadata describing the associated healthcare service. When a user selects a particular healthcare service from the list of healthcare service recommendations, the method may include interconnecting a client device with a computing system associated with the particular healthcare service.

18 Claims, 8 Drawing Sheets

INTELLIGENT TRIAGING ENGINE

CROSS-REFERENCE TO RELATED APPLICATIONS

This application claims priority to and the benefit of the filing date of U.S. Provisional Patent Application No. 62/253,267 entitled "Intelligent Triaging Engine," filed on Nov. 10, 2015, the entire contents of which is hereby expressly incorporated by reference.

FIELD OF THE DISCLOSURE

This disclosure relates generally to an intelligent triaging engine, in particular, to utilizing the intelligent triaging engine to unify disparate computer systems.

BACKGROUND DESCRIPTION

Many healthcare providers offer a variety of healthcare channels to patients. For example, a hospital may include an emergency treatment center, primary care physicians and web-based information offerings. Traditionally, these systems are independently operated by different computing systems. As a result, a patient must independently decide which channel of healthcare is the most appropriate for his or herself. In many cases, the patient is unaware of the different options and may end up electing to utilize a more expensive channel or one that offers more comprehensive care than needed for the currently-experienced symptoms. Further, because the different channels of healthcare traditionally exist in discrete computing environments, the patient is unable to conveniently compare and contrast different healthcare channels. Consequently, there is a need to integrate the computing systems corresponding to the various different channels of healthcare into a single triaging engine to more accurately and efficiently route the patient to the most appropriate healthcare channel.

SUMMARY

In an embodiment, a method for triaging a user may be provided. The method may be executed by one or more computer processors and comprise (1) receiving, from a client device via a communication network, one or more indications of medical symptoms; (2) analyzing, by the one or more computer processors, the indications of medical symptoms to determine a diagnosis; (3) assigning, by the one or more computer processors, the diagnosis a severity category from a plurality of severity categories; and (4) when the diagnosis is assigned a non-emergency severity category (i) analyzing, by the one or more computer processors, a database of user data, the user data indicating a history of interactions by the user, (ii) generating, by the one or more computer processors, a list of healthcare service recommendations, the list of healthcare service recommendations ordered based upon the user data, (iii) corresponding listed healthcare service recommendations to filterable and/or sortable metadata, and (iv) transmitting, to the client device via the communication network, the list of healthcare service recommendations, the transmission causing the list of healthcare service recommendations to be displayed on the client device.

In another embodiment, an intelligent triaging engine may be provided. The intelligent triaging engine may include (i) one or more computer processors; (ii) one or more transceivers; (iii) a first interconnect with a medical diagnosis engine configured, the medical diagnosis engine configured to (a) receive one or more indications of medical symptoms, (b) analyze the indications of medical symptoms to determine a diagnosis, and (c) assign the diagnosis a severity category from a plurality of severity categories; and (iv) one or more non-transitory memories coupled to the one or more processors. The one or more non-transitory memories may include computer executable instructions stored therein that, when executed by the one or more processors, cause the intelligent triaging engine to (1) receive, via the one or more transceivers, an indication to launch a triage interface; (2) responsive to receiving the indication to launch the triage interface; launch, by the one or more processors and via the interconnect, the medical diagnosis engine; (3) receive, via the interconnect, the diagnosis and the severity category of the diagnosis generated by the medical diagnosis engine; (4) analyze, by the one or more processors, a database of user data, the user data indicating a history of user interactions; (5) correspond, by the one or more processors, listed healthcare service recommendations to filterable and/or sortable metadata; (6) generate, by the one or more processors, a list of healthcare service recommendations, the list of healthcare service recommendations arranged based upon the user data; and (7) transmit, via the one or more transceivers, the list of healthcare service recommendations.

In yet another embodiment, a non-transitory computer-readable storage medium storing processor-executable instructions may be provided. When executed, the instruction may cause one or more processors to (1) receive, via a communication network, an indication to launch a triage interface; (2) responsive to receiving the indication to launch the triage interface; launch, by the one or more processors, a medical diagnosis engine; (3) receive, from the medical diagnosis engine, a diagnosis and the severity category of the diagnosis generated by the medical diagnosis engine; (4) analyze, by the one or more processors, a database of user data, the user data indicating a history of user interactions; (5) correspond, by the one or more processors, listed healthcare service recommendations to filterable and/or sortable metadata; (6) generate, by the one or more processors, a list of healthcare service recommendations, the list of healthcare service recommendations arranged based upon the user data; and (7) transmit, via the communication network, the list of healthcare service recommendations.

DETAILED DESCRIPTION OF THE EMBODIMENTS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

In embodiments described below, an intelligent triaging engine interconnects a client device with a plurality of healthcare services and their corresponding computer systems. The intelligent triaging engine may then interact with the client device to ensure that the user is directed to the most appropriate healthcare services based on a determined medical diagnosis.

For example, the healthcare services may include a doctor appointment, a telemedicine call, or a doctor house call. In the case of a doctor appointment, interconnecting the client device with the doctor's healthcare computing system may enable the user to schedule an appointment with the doctor. It should be appreciated that some particular doctors may outsource their scheduling to third party appointment scheduling service. In these scenarios, interconnecting the client device with the particular doctor's computing system may include interconnecting the client device with the third party appointment scheduling service. In the case of a telemedicine call, interconnecting the client device with the telemedicine provider may include facilitating the telemedicine call on the client device and/or scheduling a telemedicine call in the future. Similarly, in the case of a doctor house call, interconnecting the client device with the doctor house call provider may include facilitating the scheduling of the doctor house call in the future.

As another example, a healthcare service may include a visit to one of a plurality of health clinics. In this example, interconnecting the client device with the health clinic provider may enable the user to schedule an appointment at a preferred health clinic. This preference may additionally be based on proximity to a current and/or residential location, as well as availability of each particular health clinic.

In yet another example, a healthcare service may include a medical product locator. To this end, some diagnoses may be treated by over-the-counter (OTC) medications or other OTC medical products (e.g., ice packs, heat pads, etc.). Thus, interconnecting the client device with the medical product locator may enable the user to view a nearby location at which the user may purchase the recommended OTC medical product.

System Overview

Figure 1:
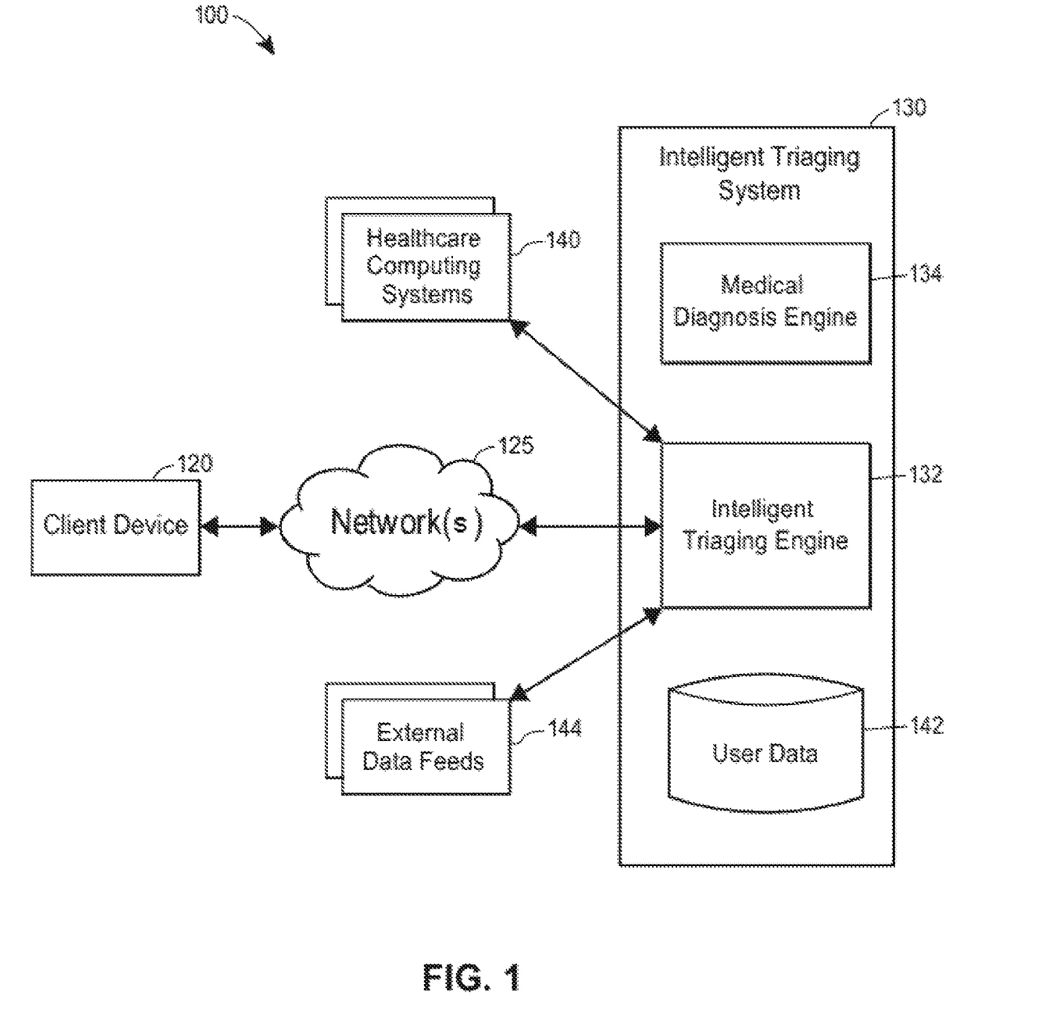
FIG. 1 illustrates an example triaging system that utilizes the intelligent triaging engine.

Referring to FIG. 1, illustrated is an example environment 100 for the execution of an intelligent triaging process. The environment 100 may include a client device 120 that interacts with an intelligent triaging system 130 via one or more communication networks 125. The client device 120 may be a computer, a mobile phone, a tablet or any other electronic device capable of wireless communications. It should be appreciated that although only environment 100 only depicts the client device 120, other embodiments may include any number of client devices, for example, a plurality of different users may interact with respective client devices 120 to communicate with the intelligent triaging system 130. A user may operate the client device 120 to launch an internet browser application and navigate to a website that facilitates access to the intelligent triaging system 130. In other embodiments, the user may operate the client device 120 to launch a standalone application dedicated to interfacing with the intelligent triaging system 130. The network 125 may be a local area network (LAN), a wide area network (WAN), or a mobile data network (e.g., LTE, EVDO, GSM and the like), for example.

As it is user herein, the word "user" refers to the operator of the client device 120. Additionally, the word "patient" refers to a person experiencing medical symptoms. That said, any use of the word "user" contemplates both the scenario in which the user is the patient and the scenario in which the user is assisting the patient in the intelligent triaging process. As a result, although both the words "user" and "patient" may be used in the same sentence, the terms "user" and "patient" may still refer to the same person.

The intelligent triaging system 130 may include different engines dedicated to performing specific tasks. For example the intelligent triaging system 130 may include an intelligent triaging engine 132 for overseeing the execution of the triaging process, and a medical diagnosis engine 134 for generating a diagnosis based upon one or more indications of medical symptoms. As it is user herein, the term "engine" refers to a set of non-transitory computer instructions configured to execute a specific function, as well as any computer processors on which the instructions are executed. It should be appreciated that in some scenarios, the same computer processor may execute instructions associated with two or more different engines. In this scenario, the computer processor may be considered a part of both the intelligent triaging engine 132 and the medical diagnosis engine 134. In addition to the aforementioned engines, the intelligent triaging system 130 may also include a database of user data 142. The intelligent triaging engine 132, the medical diagnosis engine 134, and the user database 142 may all be interconnected via a local and/or private intranet network. For example, the interconnections may be facilitated via a Ethernet, a communication bus, Wi-Fi, and/or any other suitable communication means within an intranet.

The intelligent triaging engine 132 may interface with the client device 120 via the networks 125 and oversee the execution of the intelligent triaging process. To this end, the intelligent triaging engine 132 may ensure that both the medical diagnosis engine 134 is accessed upon receiving an indication from the client device 120. Additionally, the intelligent triaging engine 132 may analyze outputs of the medical diagnosis engine 134 to generate a list of recommended healthcare services. The intelligent triaging engine 132 may then transmit the generated list of healthcare service recommendations to the client device 120 via the networks 125.

According to aspects, once the user selects a recommended healthcare service, the intelligent triaging engine 132 may interface with the plurality of healthcare computing systems 140 to interconnect the client device 120 and the healthcare computing system corresponding to the selected healthcare service. As it is used herein, the term "interconnect" as it relates to interconnecting the client device 120 and one or more of the healthcare computing systems 140, includes, but is not limited to, the provision to the client device 120 of an Application Program Interface (API) corresponding to the selected healthcare service. In some embodiments, the web browser or client application may download an API associated with each of the healthcare computing systems 140 upon accessing the website or downloading the application, respectively. The interconnection may also occur via a web service and/or plugin facilitated by the internet browser. In these embodiments, it should be appreciated that the "interconnecting" occurred prior to the selection of the healthcare service. In other embodiments, the API may be transmitted only after the user has selected a healthcare service from the list of healthcare service recommendations to reduce the file size of the web site and/or application. It should be understood that the transmitted API may be utilized to generate an interface on the client device that guides the user through scheduling the healthcare service and/or providing a telemedicine call. Additionally, this usage of the term "interconnect" may include the provision of an IP address corresponding to the selected healthcare service. In these embodiments, the client device 120 may communicate directly with the healthcare computing systems corresponding to the selected healthcare service via the provided IP address. Alternatively, the intelligent triaging engine 132 may withhold the IP address corresponding to the healthcare computing systems 140 to limit access to the healthcare computing systems 140. In these scenarios, the intelligent triaging engine 132 may act as a relay between the client device 120 and the healthcare computing services 140.

The medical diagnosis engine 134 may be configured to receive data indicative of medical symptoms and output a possible diagnosis and/or diagnosis severity. For example, the medical diagnosis engine 134 may receive inputs indicating the patient is experiencing stomach cramps and a dull pain. In response, the medical diagnosis engine 134 may diagnose the patient as experiencing gas pains. The medical diagnosis engine 134 may further categorize gas pains as a non-emergency severity. According to certain aspects, the medical diagnosis engine 134 may be configured to communicate directly with the client device 120 to receive the medical symptom data.

The user database 142 may store a plurality of data associated with a plurality of users, including the user of the client device 120. The user data may include indications of preferences associated with the user (e.g., the user prefers a particular orthopedist) as well as any previous selections made through past interactions with the intelligent triaging system 130. The user data may also include insurance information associated with the user and/or patient. Additionally, the user data may include geopositioning data representative of the user's current and/or residential location. The geopositioning data may be utilized to recommend healthcare services proximate to a current and/or residential location. The geopositioning data may also be utilized to generate localized preference trends to tailor recommendations in specific geographic regions. For example, the user data may indicate that users residing in New York City disproportionately prefer to utilize a doctor house call service.

The intelligent triaging system 130 may also be configured to receive a plurality of external data feeds 144. The external data feeds 144 may comprise a plurality of streams of data generated by a third parties. For example, the external data feeds 144 may include a data feed indicative of weather patterns, a data feed indicative of levels of allergens, a data feed of health outbreak alerts (such as those provided by the Center for Disease Control), as well as any other relevant data feeds generated by third parties. According to aspects, any data received from the external data feeds 144 may be stored in the user database 142 and/or another (not depicted) data storage component of the intelligent triaging system 130.

Intelligent Triaging

Figure 2:
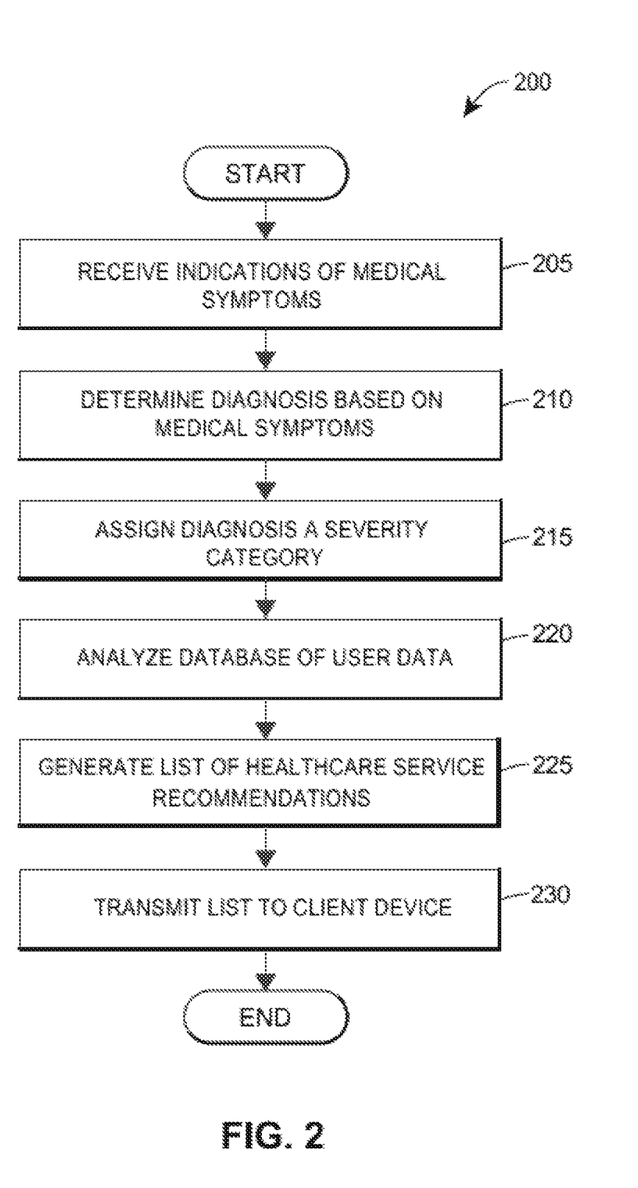
FIG. 2 is a flow diagram of an example method for intelligently triaging patients that can be implemented in the intelligent triaging system in FIG. 1.

FIG. 2 illustrates a flow diagram of an example method 200 for intelligently triaging patients. The method 200 may be implemented in an intelligent triaging system, such as the intelligent triaging system 130 described with respect to FIG. 1.

To begin, the intelligent triaging system may receive a plurality of indications of medical symptoms from a client device, such as the client device 120 (block 205). The indications may describe a plurality of medical symptoms a patient is experiencing. For example, the medical symptoms may include nausea, localized pain or discomfort, bleeding or swelling, localized burning, or any other type of medical symptom. It should be appreciated that a user may transmit any number of medical symptoms experienced by the patient. As an example, the user may interact with a virtual assistant and/or a chat bot that engages the user in an interactive conversation in which the user describes the medical symptoms experienced by the patient. In this example, a natural language processor may analyze the conversation to generate one or more indications of medical symptoms. In some embodiments, the indications may be a string of characters textually indicating the medical symptom. In other embodiments, the indications may be a reference number to query an index of medical symptoms.

The intelligent triaging system may then determine a possible diagnosis for the patient based upon the received indications of medical symptoms (block 210). To this end, the intelligent triaging system may compare the set of medical symptoms to a database of all medical diagnoses. Each medical diagnosis may correspond to a plurality of medical symptoms that are present, or typically present, for a patient having the medical diagnosis. If the set of received medical symptoms align with those associated with a particular diagnosis, then the intelligent triaging system may determine that the possible diagnosis is the particular diagnosis. It should be appreciated that in some scenarios, after receiving the set of medical symptoms, more than one medical diagnosis may be possible. In these scenarios, the intelligent triaging system may transmit a question to the client device to more accurately diagnose the patient. Similarly, the intelligent triaging system may transmit a list of possible diagnoses to the client device such that the user may select the possible diagnosis the user believes is most accurate.

After determining the possible diagnosis, the intelligent triaging system may assign the possible diagnosis a severity category (block 215). The intelligent triaging system may be associated with a plurality of severity categories. For example, the intelligent triaging system may utilize emergency and non-emergency categorizations. In this example, an emergency severity may indicate that the patient needs immediate medical attention; whereas the non-emergency severity may indicate that the patient may wait some time before receiving healthcare. Similarly, the intelligent triaging system may utilize acute and non-acute categorizations. In these embodiments, the acute severity may indicate that the patient is experiencing a medical condition that can be readily treated (e.g., a broken bone, bleeding, trauma, etc.); whereas a non-acute severity may indicate that the patient is experiencing a chronic medical condition (e.g., mental health problems, arthritis, etc.). The intelligent triaging system may categorize each diagnosis in the database of all possible medical diagnoses with the severity category labels. Thus, when the intelligent triaging system determines the possible diagnosis, the intelligent triaging system may assign the severity category by querying the corresponding severity category labels.

At this point, the intelligent triaging system has determined the possible diagnosis of the patient and a severity of the possible diagnosis. The intelligent triaging system may then begin the process of providing a list of healthcare service recommendation to the user. In an example, if the intelligent triaging system determined that the possible diagnosis is of an emergency severity, the intelligent triaging system may generate a recommendation that the user dials 911 or contacts another emergency service provider (e.g., a hospital, emergency treatment center, etc.). The recommendation may include a list of emergency service providers closest to the current location of the client device (as determined based upon geopositioning data received from the client device).

Similarly, the intelligent triaging system may determine the possible diagnosis is of a non-emergency severity category. In this scenario, the intelligent triaging system may analyze a database of user data, such as the user database 142, to tailor recommendations to the specific user (block 220). One way the recommendations may be tailored is by weighting and/or scoring a plurality of factors associated with the patient and/or user. One such factor may be an insurance score. To this end, the intelligent triaging system may analyze the user data to determine an insurer of the patient. The intelligent triaging system may give a higher insurance weight to healthcare services, such as counseling services and/or health care provider services, that are "in-network" for the insurer of the patient. Conversely, "out-of-network" healthcare services may been given a lower insurance weight. Insurance data may also be used to determine that the patient is uninsured and assign a higher insurance weight to healthcare services in which insurance does not significantly alter the price of the healthcare service.

Another factor may be a user preference score. Accordingly, the user data may indicate a plurality of user preferences corresponding to the patient. For example, the user data may indicate that a particular doctor is the patient's specialist for a type of condition corresponding to the possible diagnosis (e.g., the patient has a history with a particular gastroenterologist for acid reflux). Thus, if the possible diagnosis is for a condition normally treated by the specialist, the patient's existing specialist may be give a higher user preference weight. Similarly, if the possible diagnosis may be treated by a general physician, then the patient's primary care physician may be given a higher user preference weight.

Because different healthcare services may be offered at vastly different costs to the patient, a price score may be another factor. In an example, a telemedicine call may be provided at a lower cost than a doctor visit to the patient's home. That said, not all customers prefer the cheapest healthcare service; some customers may prefer more expensive and/or comprehensive healthcare services. Thus, the intelligent triaging system may analyze past selections made by the patient when previously interacting with the intelligent triaging system to understand the patient's cost preferences, particularly if the past interactions relate to a similar diagnosis as the current possible diagnosis. If the patient preferred healthcare services offered at a particular price point, then the intelligent triaging system may give a higher price weight to those healthcare services offered at that price point.

Another factor may be a location-based score. To this end, the client device may periodically transmit geopositioning data while interacting with the intelligent triaging system. The location of the client device may then be compared with the location of a plurality of healthcare clinics. The intelligent triaging system may then determine if there are any open healthcare clinic near the location of the client device. If there is are at least one open healthcare clinic, the intelligent triaging system may assign location weights based on the relative proximity to the current location of the client device. As another example, the intelligent triaging system may then determine various preferences of other users in a similar geographical region as the client device. Accordingly, the intelligent triaging system may adjust the location weight based upon the preferences of other similarly located users.

According to aspects, the intelligent triaging system may also analyze a plurality of external data feeds (such as the external data feeds 144) to generate additional scores. For example, if an external data feed indicates that there is a strep throat breakout in the geographic region corresponding to the current or residential location of the user, and the possible diagnosis is similar to strep throat, then the patient may need an in-person healthcare service to receive a strep throat test. As a result, the intelligent triaging system may assign clinics and/or primary care physicians a higher outbreak weight and assign telemedicine a lower outbreak weight. As another example, an external data feed may indicate a high level of pollen (or any other allergen) in the current location of the client device. If the possible diagnosis is related to allergies, the intelligent triaging system may assign a higher allergy score a medical product locator services. In this example, if this user data indicates that the patient has repeatedly been diagnosed with allergies, the intelligent triaging system may additionally assign allergy specialists an even higher allergy score.

Although the foregoing identifies several factors, it should be understood that any number of additional or alternative factors may be identified and/or scores, including those discussed elsewhere herein. Once the intelligent triaging system determines the scores for each factor, the intelligent triaging system may combine the individual scores into an overall score. For example, the intelligent triaging system may use a machine learning algorithm to determine the most accurate way to combine the various factor scores into the overall score based upon the particular user and/or diagnosis. It should be understood that the machine learning algorithm may be updated based up the user selecting (or not selecting) each healthcare service recommendation.

Once the intelligent triaging system has analyzed the user data to determine the overall score for all of the healthcare services, the intelligent triaging system may generate a list of healthcare service recommendations (block 225). The list of healthcare service recommendations may represent a compilation of the most highly-scored healthcare services. To this end, the list of healthcare service recommendation may order the healthcare services with the highest overall score at the beginning of the list and continue in decreasing order until a cutoff overall score is reached and/or the list reaches a maximum size. It should be appreciated that due to the reliance on patient- and/or user-specific user data, two patients experiencing the same medical symptoms in the same location may cause the intelligent triaging system to generate different lists of healthcare service recommendations.

Additionally, the intelligent triaging system may correspond each recommendation in the list of healthcare service recommendations with a plurality of metadata describing the recommendation. For example, the metadata may include a name of a provider of the healthcare service, a type of healthcare service (clinic, telemedicine, medical product locator, etc.), a cost of the healthcare service, an availability of the healthcare service, and/or any of the individual scores determined via the analysis of the user data. Consequently, a user interface may be configured to sort and/or filter the list of healthcare service recommendations based upon a selected type of metadata.

After the list of healthcare service recommendations is generated, the intelligent triaging system may transmit the list to the client device (block 230). As a result, the client device may display an interface providing a selectable interface element associated with each healthcare service recommendation. In some scenarios, the user may be required to scroll and/or take other navigational actions to view less preferred recommendations. If the user selects a particular healthcare service recommendation, the client device may then transmit an indication of the selected healthcare service to the intelligent triaging system. As a result, the intelligent triaging system may interconnect the client device with a computing system corresponding to the selected healthcare service. Additionally, the intelligent triaging system may update the user data associated with the patient to include an indication of the user selection.

In some embodiments, after the intelligent triaging system interconnects the client device with the computing systems of the selected healthcare service, the intelligent triaging server may receive an indication that the healthcare service has been successfully provided and/or administered to the patient. For example, in the case of a telemedicine call, this may include an indication that the telemedicine call has been terminated. As part of indication that the healthcare service has been provided to the patient, the intelligent triaging system may receive an indication of a diagnosis as determined by the doctor providing the healthcare service. It should be appreciated that this doctor-determined diagnosis may not be the same diagnosis as the possible diagnosis determined by the intelligent triaging system.

Upon receiving the doctor-determined diagnosis, the intelligent triaging system may query a database of medical diagnoses to determine an OTC product to treat and/or alleviate symptoms associated with the doctor-determined diagnosis. In some embodiments, this database of medical diagnoses utilized to generate the possible diagnosis may additionally include this OTC product recommendation. According to aspects, the intelligent triaging system may then interact with the computing systems corresponding to the medical product locator healthcare service to generate a list of nearby locations at which the recommended OTC product may be purchased. The intelligent triaging system may then transmit the list of nearby locations to the client device for display. In some embodiments, the intelligent triaging system may identify one or more medical products prescribed to the patient. In these embodiments, the intelligent triaging system may avoid recommending an OTC product associated with harmful interactions with one or more of the prescribed medical products.

Additionally or alternatively, the intelligent triaging system may provide one or more articles to the user in order to provide additional information relating to the possible diagnosis and/or the doctor-determined diagnosis. In one embodiment, the database of medical diagnoses associates the stored diagnoses with one or more articles that, for example, provide background knowledge about the diagnosis, tips on how to cope with the diagnosis, developments in treating the diagnosis, and so on. In one scenario, the articles are curated and/or generated by a provider of the intelligent triaging system.

Figure 3:
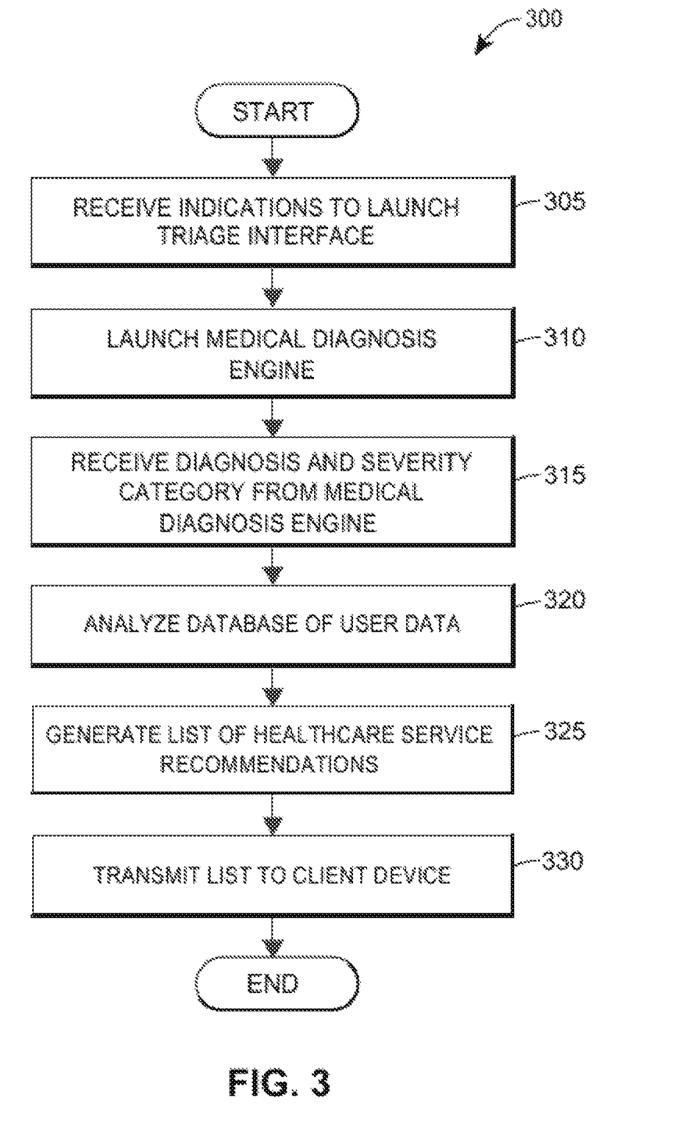
FIG. 3 is a flow diagram of an example method for intelligently triaging patients that can be implemented in the intelligent triaging engine of FIG. 1.

FIG. 3 illustrates a flow diagram of an example method 300 for intelligently triaging patients. The method 300 may be implemented in an intelligent triaging engine, such as the intelligent triaging engine 132 described with respect to FIG. 1.

To begin, the intelligent triaging engine may receive an indication to launch a medical triaging interface (block 305). To this end, a client device (such as the client device 120) may display an interface associated with the intelligent triaging engine. The interface may include an interface element to indicate that the user is attempting to begin the intelligent triaging process. When this interface element is selected by the user, the client device may transmit the indication to the intelligent triaging engine.

Upon receiving the indication, the intelligent triaging engine may cause the a medical diagnosis engine (such as the medical diagnosis engine 134) to launch (block 310). For example, the intelligent triaging engine may interface with the medical diagnosis engine via an API or web service. The API or web service may include a function that launches the medical diagnosis engine. Thus, in order to launch the medical diagnosis engine, the intelligent triaging engine may transmit the launch instruction via an interconnect between the intelligent triaging engine and the medical diagnosis engine (e.g., a communication bus, a wireless communication link, or any other suitable means for transmitting instructions between to computing engines). In some embodiments, the launch command may require the provision of an IP address associated with the client device as an input. In these embodiments, the intelligent triaging engine may include in the launch command the IP address of the client device, as determined, for example, by the address from which the indication to launch the medical triaging interface was submitted.

In response to receiving the launch command, the medical diagnosis engine may communicate directly with the client device to determine a possible diagnosis of the patient. To this end, the medical diagnosis engine may be configured to perform actions substantially similar to those described with respect to blocks 205-215 of the method 200. After the medical diagnosis engine finishes performing those actions, the intelligent triaging engine may receive an indication of the possible diagnosis and a severity category of the possible diagnosis from the medical diagnosis engine (block 315). These indications may be received via the same interconnect via which the launch instruction was transmitted. After receiving the indication of the possible diagnosis and the corresponding severity category, the intelligent triaging engine may analyze user data associated with the user and/or patient (block 320), generate a list of healthcare service recommendations (block 325), and transmit the generated list to the client device (block 330). To this end, the intelligent triaging engine may perform substantially similar actions as those described with respect to blocks 220-230 of the method 200.

Example User Interfaces

With reference to FIGS. 4-8, the intelligent triaging process is described with respect to user interfaces displayed on a client device, such as the client device 120. Although the following example interfaces are displayed on the client device, it should be appreciated that the computer-readable instructions that implement the following example interfaces may have been generated by an operator of an intelligent triaging system (such as the intelligent triaging system 130) and distributed to the client device via a web browser and/or application store. Thus, any action associated with the following exemplary interfaces includes both the performance on the client device and the generation, compilation, and/or distribution of computer-readable instructions by the operator to enable said performance.

Figure 4:
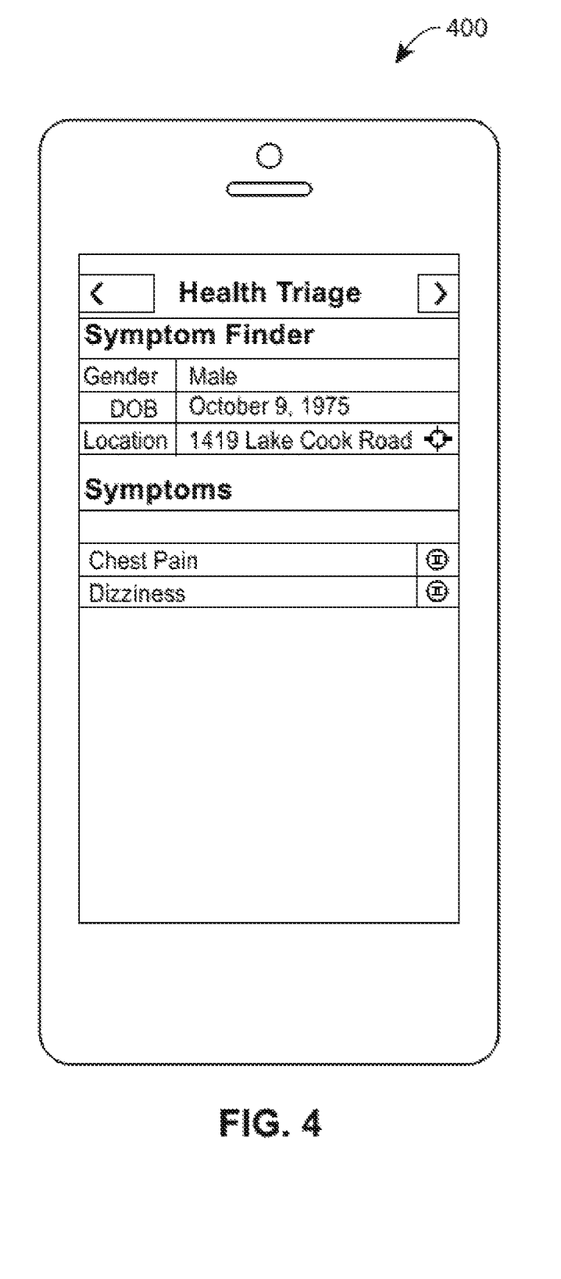
FIG. 4 illustrates an example medical diagnosis interface for inputting medical symptom data displayed on the client device of FIG. 1.

FIG. 4 illustrates an example medical diagnosis interface 400 for inputting medical symptom data. The interface 400 may provide the ability for a user to input demographic and/or geographic data associated with a patient. In some embodiments, the demographic and/or geographic data may be prepopulated based upon stored user data or sensor data, respectively. The interface 400 may also be configured to enable the user to manually modify any prepopulated demographic and/or geographic data.

Additionally, the interface 400 may be configured to enable the user to enter a plurality of medical symptoms associated with the patient. For example, as depicted in FIG. 4, the medical symptoms may include "chest pain" or "dizziness." The interface 400 may also provide an interface element that, when selected, causes the display of an additional interface to enter an additional medical symptom (not depicted). This additional interface may enable the user to enter a medical symptom via a text entry box. The additional interface may also depict an image of a human body and enable the user to select an area of the body experiencing the symptom. Upon selection of an area of the body, the additional interface may display a list of symptoms associated with that particular area. The interface 400 may be configured to transmit any demographic, geographic, or medical symptom data to the intelligent triaging system automatically upon entry and/or upon selection of an interface element configured to cause the transmission of the demographic, geographic, and/or medical symptom data.

Figure 5:
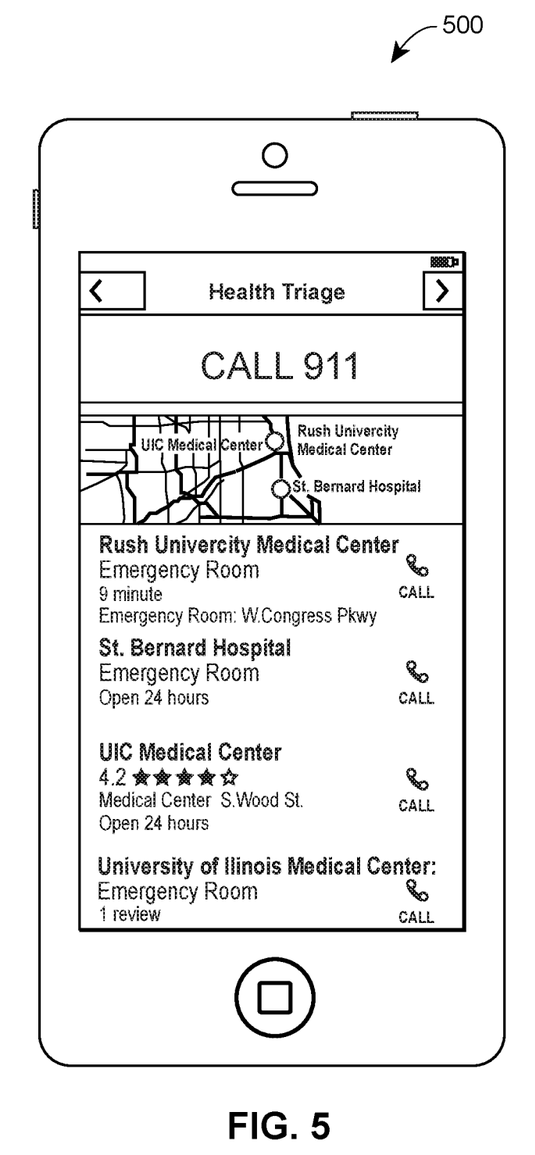
FIG. 5 illustrates an example interface, in response to determining an emergency diagnosis, for displaying a list of recommended healthcare services on the client device of FIG. 1.

FIG. 5 illustrates an example interface 500, in response to determining an emergency diagnosis, for displaying a list of recommended healthcare services. For example, the interface 500 may be configured to be displayed if the medical symptoms entered into the interface 400 are indicative of the patient experiencing a heart attack. As depicted, the interface 500 may include a recommendation to call 911. In an aspect, if the user selects the call 911 region of the interface 500, the interface 500 may be configured interact with a dialer on the client device to originate a call to 911.

Additionally, as depicted in FIG. 5, the interface 500 may include recommendations that the patients visit an emergency room. As part of the recommendation, the interface 500 may be configured to display a map including the current location of the client device and/or recommended emergency rooms. Additionally, the recommendation for each emergency room may include information describing the particular emergency room, such as, for example, a name of the emergency room, a time and/or distance from the current location of the client device, a rating, hours of operation, and/or a phone number. Upon the user selecting a particular recommended emergency room, the interface 500 may be configured to interact with a dialer on the client device to originate a call to the selected emergency room and/or to launch a navigation client to provide directions to the emergency room from the current location of the client device.

Figure 6:
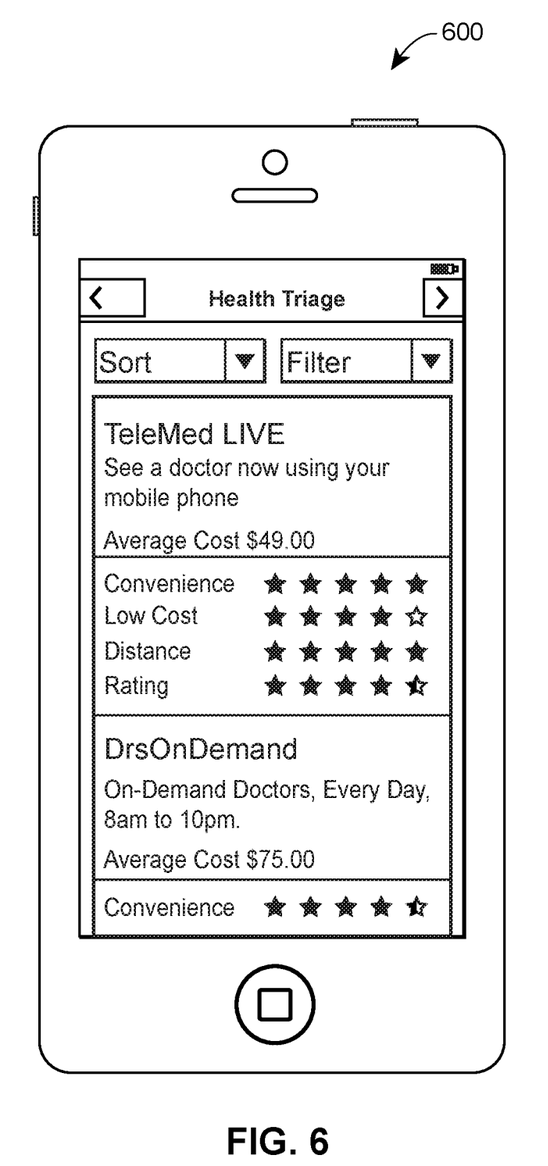
FIG. 6 illustrates an example interface, in response to determining a non-emergency diagnosis, for displaying a list of recommended healthcare services on the client device of FIG. 1.

FIG. 6 illustrates an example interface 600, in response to determining a non-emergency diagnosis, for displaying a list of recommended healthcare services. More particularly, the interface 600 may be configured to display the list of recommended healthcare services generated by the intelligent triaging system in response to receiving the medical symptom data transmitted by the client device. To this end, the list of recommended healthcare services may display the healthcare services with a higher overall score (as determined by the intelligent triaging system) above healthcare services with lower overall scores. Due to display size constraints, the interface 600 may only be able to display a portion of the full list of healthcare service recommendations at any one time. Thus, the interface 600 may be configured to enable the user to scroll (e.g., by the user swiping up or down on the interface 600) to view the other healthcare service recommendations.

For each healthcare service recommendation displayed by the interface 600, the interface 600 may be configured to display a plurality of information associated with the corresponding healthcare service. More particularly, the interface 600 may cause the client device to analyze metadata associated with each healthcare service recommendation to display the corresponding information. For example, the metadata may include a name, a cost, and/or an availability of the healthcare service. As a result, the interface 600 may be configured to display the name, cost, and/or availability of each healthcare service recommendation. Additionally, the metadata may include a plurality of ratings corresponding to each healthcare service recommendation. Thus, the interface 600 may be configured to display the plurality of ratings associated with each healthcare service recommendation. As an example, as depicted in FIG. 6, the ratings may include a rating for convenience, low cost, distance, and/or an overall rating.

In an aspect, the interface 600 may be configured such that each healthcare service recommendation is selectable. When the user selects a particular healthcare service recommendation, the client device may become interconnected to a computing system associated with the corresponding healthcare service. For example, if the user selects the depicted TeleMed LIVE healthcare service recommendation, the client device may become interconnected with the TeleMed LIVE computing systems to facilitate the provision of the corresponding mobile telemedicine service. In an embodiment, the selection of the particular healthcare service recommendations causes the client device to transmit an indication to the intelligent triaging system. In response, the client device may receive an API and/or an IP address of the computing systems associated with the corresponding healthcare service. In another embodiment, a web browser may be directed to a web service and/or download a plugin associated with the corresponding healthcare service. As a result, in response to receiving a selection of a particular healthcare service recommendation, the interface 600 may cause an interface generated and/or associated with the computing systems associated with the corresponding healthcare service to be displayed on the client device.

Figure 7:
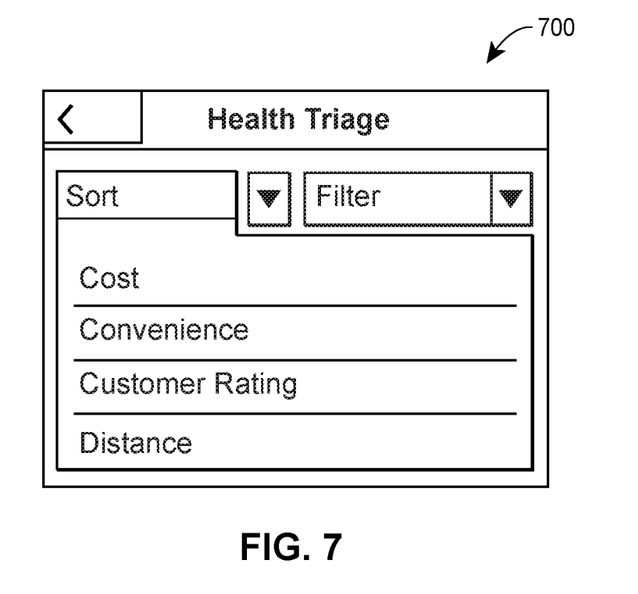
FIG. 7 illustrates an example interface for sorting a list of recommended healthcare service displayed on the client device of FIG. 1.

The interface 600 may be further configured to provide interface elements that enable a user to sort the list of healthcare service recommendations. FIG. 7 illustrates an example interface 700 for sorting a list of recommended healthcare services. For example, the interface 700 may be displayed by the client device in response to the user selecting the "Sort" drop down menu displayed by the interface 600. The interface 700 may be configured to display a plurality of criteria by which the list of healthcare service recommendations may be sorted. In some embodiments, the sort criteria may be the same as the ratings categories associated with each healthcare service recommendation. When the user selects a particular sort criteria from the interface 700, the list of healthcare service recommendations displayed by the interface 600 may be sorted in accordance with the sort criteria. For example, the DrsOnDemand healthcare service may correspond to a higher Low Cost rating than the TeleMed LIVE healthcare service. As a result, when the user selects the Low Cost sort criteria from the interface 700, the list of healthcare service recommendations displayed by the interface 600 may display the DrsOnDemand recommendation above the TeleMed LIVE recommendation.

Figure 8:
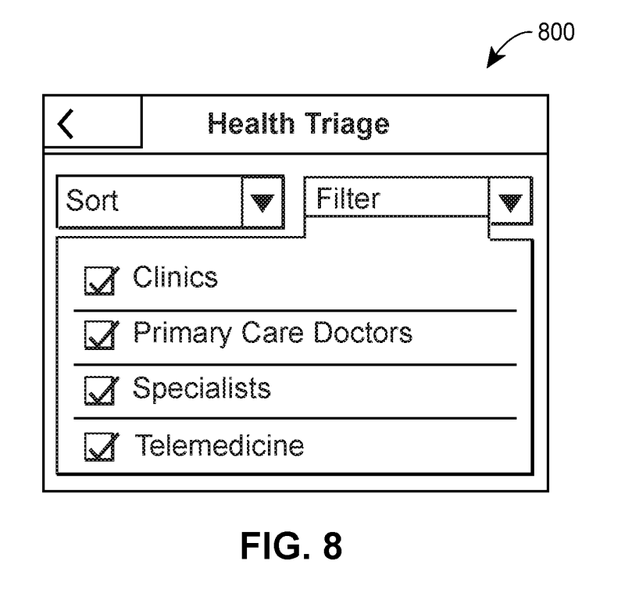
FIG. 8 illustrates an example interface for filtering a list of recommended healthcare service displayed on the client device of FIG. 1.

Additionally, the interface 600 may be configured to provide interface elements that enable a user to filter the list of healthcare service recommendations. FIG. 8 illustrates an example interface 800 for filtering a list of recommended healthcare services. For example, the interface 800 may be displayed by the client device in response to the user selecting the "Filter" drop down menu displayed by the interface 600. The interface 800 may be configured to display a plurality of types of healthcare services by which the list of recommended healthcare service may be filtered. For example, as depicted in FIG. 8, the filterable types of healthcare service may include clinics, primary care doctors, specialists, and/or telemedicine.

According to aspects, the interface 600 may only be configured to display healthcare service recommendation corresponding to a particular type of healthcare service (e.g., those that are checked in the interface 800). When the user selects a particular type of healthcare service from the interface 800, the interface 800 may toggle a filter state of the particular type of healthcare service. For example, because, as displayed in FIG. 8, the Telemedicine type is checked, if the user selects Telemedicine from the drop down list, the Telemedicine type may become unchecked. As a result, the list of healthcare service recommendations displayed by the interface 600 may be filtered to remove any Telemedicine recommendations. In the example depicted in FIG. 6, this may cause the TeleMed LIVE healthcare service recommendation to be filtered out of the displayed list of healthcare recommendations. Similarly, if the user were to select the Telemedicine type a second time (i.e., causing Telemedicine to become checked again), the TeleMed LIVE healthcare service recommendation may once again be displayed by the interface 600.

Hardware Description

Figure 9:
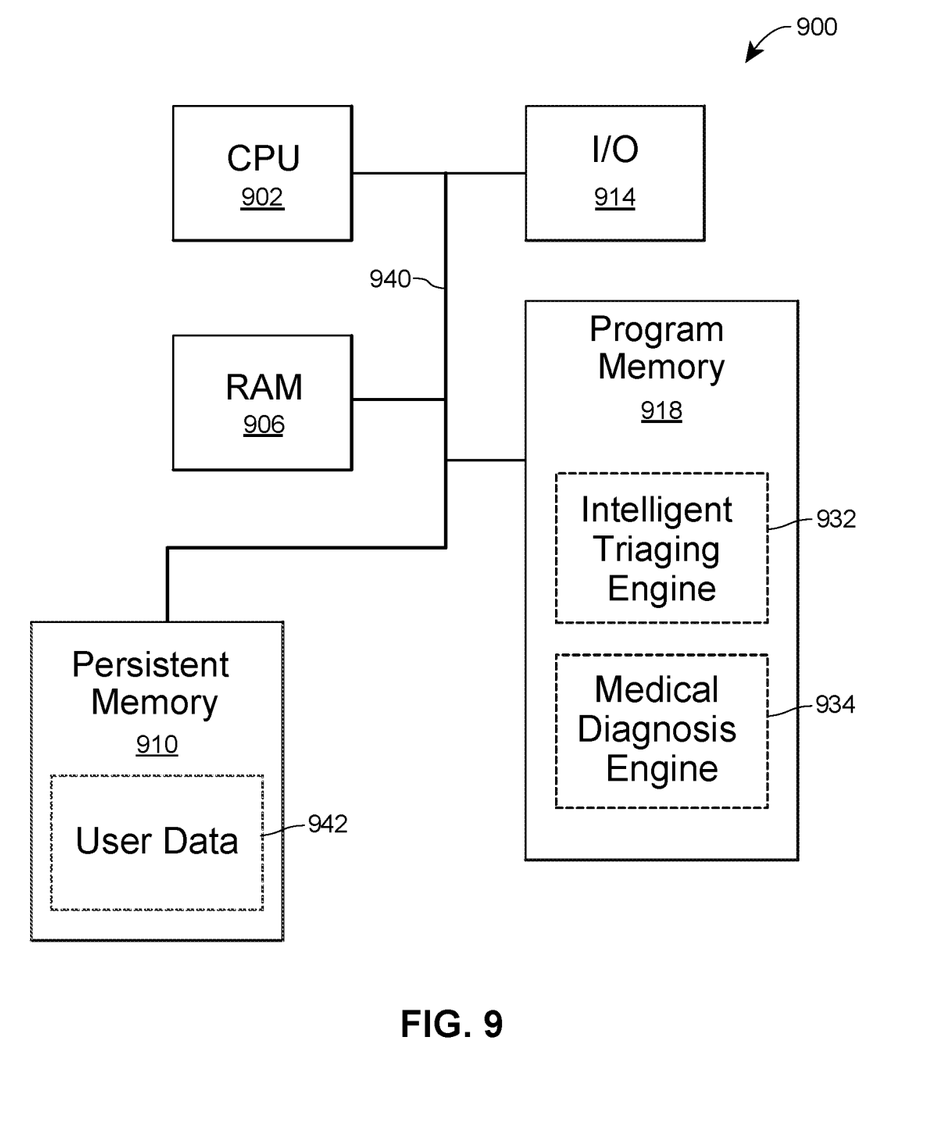
FIG. 9 illustrates an example computing device in which the intelligent triaging system of FIG. 1 is implemented, according to an embodiment.

FIG. 9 illustrates a diagram for an example intelligent triaging system 900 (such as the intelligent triaging system 130 as discussed with respect to FIG. 1) in which the functionalities as discussed herein may be implemented. The intelligent triaging system 900 includes one or more process depicted as a central processing unit (CPU) 902. During operation, the CPU 902 executes instructions stored in a program memory module 918 coupled to the CPU 902 via a system bus 940. In some implementations, the program memory module 918 is implemented in a random access memory (RAM) module 906, a persistent memory module 910, or both. The program memory module 918 may also store computer-readable instructions that regulate the operation of the intelligent triaging system 900. One set of instructions may be an intelligent triaging engine 932 that contains instructions to regulate the intelligent triaging process and generate a list of healthcare service recommendations, as discussed elsewhere herein. Another set of instructions may be a medical diagnosis engine 934 that contains instructions to determine a possible diagnosis and/or severity category thereof based upon a set of medical symptoms, as discussed elsewhere herein. The sets of instructions may be implemented in any desired language, and may be implemented as machine code, assembly code, byte code, interpretable source code or the like (e.g., via C, C++, Java, Actionscript, Objective-C, Javascript, CSS, XML). It should be appreciated that the program memory module 918 may store other sets of instructions, for example, an operating system that regulates communication between the various modules and/or engines contained within intelligent triaging system 900.

In addition to programs, the modules 906 and 910 may store data in a volatile or non-volatile mode, respectively. The modules 906 and 910 may further include one or more forms of fixed and/or removable memory, such as read-only memory (ROM), electronic programmable read-only memory (EPROM), RAM, erasable electronic programmable read-only memory (EEPROM), and/or other hard drives, flash memory, MicroSD cards, and others. For example, user data 942 (which may be similar to the user database 142 of FIG. 1) may be stored as data structures in the persistent memory module 918. During operation, the user data 942 may be loaded into the RAM module 906 via the system bus 940.

The intelligent triaging system 900 may further include an I/O module 914. The I/O module 914 may include components that enable the intelligent triaging system 900 to send and receive data over a wireless or wired network (such as network 125 of FIG. 1). The components may include one or more transceivers (e.g., WWAN, WLAN, WPAN, EVDO, CDMA, GSM and/or LTE transceivers) functioning in accordance with IEEE standards, 3GPP standards, or other standards. In addition to the transceivers, the I/O module 914 may include display screens, keys, buttons, touch sensitive input panels, external ports or other components that enable someone to interact with the intelligent triaging system 900, such as to upgrade the instructions contained in the intelligent triaging engine 932.

Although the intelligent triaging system 900 is shown to include one CPU 902, it should be understood that the processing may be distributed among a plurality of servers in an arrangement known as "cloud computing." For example, the processing associated with the intelligent triaging engine 932 and the processing associated with the medical diagnosis engine 934 may be executed by different servers. This configuration may provide several advantages, such as, reducing the load on any particular CPU, for example, by enabling parallel processing of instructions that can be divided into non-sequential steps. This parallel processing reduces the overall processing time required to perform the functionality described herein and improves the user experience on client devices that interact with the intelligent triaging system 900.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

What is claimed:

1. A method for intelligently triaging a user, the method executed by one or more computer processors, the method comprising:
   receiving, from a client device via a communication network, one or more indications of medical symptoms;
   analyzing, by the one or more computer processors, the indications of medical symptoms to determine a diagnosis;
   assigning, by the one or more computer processors, the diagnosis a non-emergency severity category from a plurality of severity categories;
   analyzing, by the one or more computer processors, a database of user data, the user data indicating a history of interactions by the user;
   generating, by the one or more computer processors, a list of healthcare service recommendations;
   applying, by the one or more computer processors, a machine learning algorithm to determine an overall score of each healthcare service recommendation of the list of healthcare service recommendations from one or more of a user-reference score, a price score, a location-based score, and an external-feed score for each healthcare service recommendation;

ordering, by the one or more computer processors, the list of healthcare service recommendations based upon the user data and the overall score of each healthcare service recommendation;

corresponding listed healthcare service recommendations to filterable and sortable metadata describing each healthcare service recommendation, wherein the metadata is filterable and sortable based on previous selections made by the user;

transmitting, to the client device via the communication network, the list of healthcare service recommendations and the corresponding filterable and sortable metadata, the transmission causing an interface to be displayed at the client device, wherein the interface includes the list of healthcare service recommendations and the interface includes an interface element that enables a user to filter or sort the list of healthcare service recommendations based on the corresponding filterable and sortable metadata;

receiving, from the client device via the communication network, an indication of a selected healthcare service; and interconnecting, by the one or more computer processors, the client device to a computing system associated with the selected healthcare service by provisioning an API corresponding to the selected healthcare service into the client device, wherein the API is provisioned only after the user has selected a healthcare service from the list of healthcare service recommendations to reduce file size on the client device, wherein the API is invoked by the client device to exchange data with the selected healthcare service, and wherein APIs corresponding to unselected healthcare services are not provisioned to the client device.

2. The method of claim 1, wherein interconnecting the client device to a computing system associated with the selected healthcare service further comprises:

interconnecting, by the one or more computer processors, the client device to a computing system associated with a telemedicine service; and receiving, from the computing system associated with the telemedicine service, an indication that the telemedicine service has been terminated.

3. The method of claim 2, wherein receiving the indication that the telemedicine service has been terminated further comprises:

receiving, from the computing system associated with the telemedicine service, an indication of a doctor-determined diagnosis;

based upon the doctor-determined diagnosis, querying, by the one or more computer processors, a diagnosis database to determine an over-the-counter product recommendation; and transmitting, to the client device via the communication network, the over-the-counter product recommendation.

4. The method of claim 1, further comprising:

receiving, from a second client device via the communication network, a second one or more indications of medical symptoms;

analyzing, by the one or more computer processors, the second indications of medical symptoms to determine a second diagnosis;

assigning, by the one or more computer processors, the second diagnosis an emergency severity category from the plurality of severity categories;

generating, by the one or more computer processors, a recommendation that a user of the second client device contacts an emergency service provider; and transmitting, to the second client device via the communication network, the recommendation.

5. The method of claim 1, wherein corresponding listed healthcare service recommendations to filterable and sortable metadata includes corresponding listed healthcare service recommendations to filterable metadata representative of a service type of a corresponding healthcare service, the service type being one of a clinic, a primary care physician, a specialist, telemedicine, a medical product locator, or a house call.

6. The method of claim 1, wherein corresponding listed healthcare service recommendations to filterable and sortable metadata includes corresponding listed healthcare service recommendations to sortable metadata representative of one or more ratings of a corresponding healthcare service, the ratings representative of at least one of cost, convenience, customer rating, or distance from user.

7. The method of claim 6, further comprising:

receiving, from a client device via a communication network, a plurality of insurance data;

for one or more healthcare service recommendations in the generated list, updating, by the one or more computer processors, the one or more ratings corresponding to the healthcare service based upon the received insurance data.

8. The method of claim 1, further comprising:

determining, by the one or more computer processors, that the user is near an open healthcare clinic; and generating, by the one or more computer processors, the list of healthcare service recommendations, the list of healthcare service recommendations including a recommendation that the user visits the open healthcare clinic.

9. The method of claim 1, wherein analyzing the database of user data further comprises:

analyzing, by the one or more computer processors, the database of user data, the user data indicating a plurality of preferences by other users within a geographical region including the user.

10. The method of claim 1, wherein generating the list of healthcare service recommendations further comprises:

analyzing, by the one or more computer processors, a plurality of external data feeds; and generating, by the one or more computer processors, the list of healthcare service recommendations, the list of healthcare service recommendations ordered based upon the plurality of external data feeds.

11. The method of claim 10, wherein analyzing the plurality of external data feeds further comprises:

analyzing, by the one or more computer processors, the plurality of external data feeds, the plurality of external data feeds indicative of at least one of a weather pattern, a Center for Disease Control (CDC) alert, or a concentration of one or more allergens.

12. An intelligent triaging engine comprising:

one or more computer processors;

one or more transceivers;

an interconnect with a medical diagnosis engine, the medical diagnosis engine configured to:

receive one or more indications of medical symptoms, analyze the indications of medical symptoms to determine a diagnosis, and assign the diagnosis a severity category from a plurality of severity categories; and one or more non-transitory memories coupled to the one or more computer processors, wherein the one or more non-transitory memories include computer executable instructions stored therein that, when executed by the one or more computer processors, cause the intelligent triaging engine to:
  receive, via the one or more transceivers and from a client device, an indication to launch a triage interface;
  responsive to receiving the indication to launch the triage interface, launch, by the one or more processors and via the interconnect, the medical diagnosis engine;
  receive, via the interconnect, the diagnosis and the severity category of the diagnosis generated by the medical diagnosis engine;
  analyze, by the one or more computer processors, a database of user data, the user data indicating a history of user interactions;
  correspond, by the one or more computer processors, listed healthcare service recommendations to filterable and sortable metadata describing each healthcare service recommendation, wherein the metadata is filterable and sortable based on previous selections made by the user;
  generate, by the one or more computer processors, a list of healthcare service recommendations;
  apply, by the one or more computer processors, a machine learning algorithm to determine an overall score of each healthcare service recommendation of the list of healthcare service recommendations from one or more of a user-reference score, a price score, a location-based score, and an external-feed score for each healthcare service recommendation;
  order, by the one or more computer processors, the list of healthcare service recommendations based upon the user data and the overall score of each healthcare service recommendation;
  transmit, via the one or more transceivers, the list of healthcare service recommendations and the corresponding filterable and sortable metadata, the transmission causing an interface to be displayed at the client device, wherein the interface includes the list of healthcare service recommendations and the interface includes an interface element that enables a user to filter or sort the list of healthcare service recommendations based on the corresponding filterable and sortable metadata;
  receive, via the one or more transceivers and from the client device, an indication of a selected healthcare service; and
  interconnect, by the one or more computer processors, the client device to a computing system associated with the selected healthcare service by provisioning an API corresponding to the selected healthcare service into the client device, wherein the API is provisioned only after the user has selected a healthcare service from the list of healthcare service recommendations to reduce file size on the client device, wherein the API is invoked by the client device to exchange data with the selected healthcare service, and wherein APIs corresponding to unselected healthcare services are not provisioned to the client device.

13. The intelligent triaging engine of claim 12, wherein to interconnect the client device to the computing system associated with the selected healthcare service, the instructions, when executed by the one or more computer processors, further cause the intelligent triaging engine to:
  interconnect, by the one or more computer processors, the client device to a computing system associated with a telemedicine service; and
  receive, via the one or more transceivers, an indication that the telemedicine service has been terminated.

14. The intelligent triaging engine of claim 13, wherein to receive the indication that the telemedicine service has been terminated, the instructions, when executed by the one or more processors, further cause the intelligent triaging engine to:
  receive, via the one or more transceivers, an indication of a doctor-determined diagnosis;
  based upon the doctor-determined diagnosis, query, by the one or more computer processors, a diagnosis database to determine an over-the-counter product recommendation; and
  transmit, via the one or more transceivers, the over-the-counter product recommendation.

15. The intelligent triaging engine of claim 12, wherein to correspond listed healthcare service recommendations to filterable and sortable metadata, the instructions, when executed, further cause the intelligent triaging engine to correspond listed healthcare service recommendations to filterable metadata representative of a service type of a corresponding healthcare service, the service type being one of a clinic, a primary care physician, a specialist, telemedicine, a medical product locator, or a house call.

16. The intelligent triaging engine of claim 12, wherein to correspond listed healthcare service recommendations to filterable and sortable metadata, the instructions, when executed, further cause the intelligent triaging engine to correspond listed healthcare service recommendations to sortable metadata representative of one or more ratings of a corresponding healthcare service, the ratings representative of at least one of cost, convenience, customer rating, or distance from user.

17. The intelligent triaging engine of claim 12, wherein to generate the list of healthcare service recommendations, the instructions, when executed, further cause the intelligent triaging engine to:
  analyze, by the one or more computer processors, a plurality of external data feeds; and
  generate, by the one or more computer processors, the list of healthcare service recommendations, the list of healthcare service recommendations ordered based upon the plurality of external data feeds.

18. A non-transitory computer-readable storage medium storing processor-executable instructions, that when executed cause one or more processors to:
  receive, via a communication network and from a client device, an indication to launch a triage interface;
  responsive to receiving the indication to launch the triage interface, launch, by the one or more processors, a medical diagnosis engine;
  receive, from the medical diagnosis engine, a diagnosis and a severity category of the diagnosis generated by the medical diagnosis engine;
  analyze, by the one or more processors, a database of user data, the user data indicating a history of user interactions;
  correspond, by the one or more processors, listed healthcare service recommendations to filterable and sortable metadata describing each healthcare service recommendation, wherein the metadata is filterable and sortable based on previous selections made by the user;

generate, by the one or more computer processors, a list of healthcare service recommendations;

apply, by the one or more computer processors, a machine learning algorithm to determine an overall score of each healthcare service recommendation of the list of healthcare service recommendations from one or more of a user-reference score, a price score, a location-based score, and an external-feed score for each healthcare service recommendation;

order, by the one or more computer processors, the list of healthcare service recommendations based upon the user data and the overall score of each healthcare service recommendation;

transmit, via the communication network, the list of healthcare service recommendations and the corresponding filterable and sortable metadata, the transmission causing an interface to be displayed at the client device, wherein the interface includes the list of healthcare service recommendations and the interface includes an interface element that enables a user to filter or sort the list of healthcare service recommendations based on the corresponding filterable and sortable metadata;

receive, via the communication network and from the client device, an indication of a selected healthcare service; and interconnect, by the one or more computer processors, the client device to a computing system associated with the selected healthcare service by provisioning an API corresponding to the selected healthcare service into the client device, wherein the API is provisioned only after the user has selected a healthcare service from the list of healthcare service recommendations to reduce file size on the client device, wherein the API is invoked by the client device to exchange data with the selected healthcare service, and wherein APIs corresponding to unselected healthcare services are not provisioned to the client device.

* * * * *